United States Patent
Agorku et al.

(10) Patent No.: US 12,221,630 B2
(45) Date of Patent: Feb. 11, 2025

(54) CELL CULTURE MEDIUM AND METHOD FOR GENERATION OF EPITHELIAL ORGANOIDS FROM EPITHELIAL STEM CELLS

(71) Applicant: MILTENYI BIOTEC B.V. & CO. KG, Bergisch Gladbach (DE)

(72) Inventors: David Joel Agorku, Bergisch Gladbach (DE); Olaf Thorsten Hardt, Bergisch Gladbach (DE); Andreas Bosio, Cologne (DE); Kristin Becker, Bergisch Gladbach (DE); Dominik Eckardt, Bergisch Gladback (DE)

(73) Assignee: MILTENYI BIOTEC B.V. & CO. KG, Bergisch Gladbach (DE)

( * ) Notice: Subject to any disclaimer, the term of this patent is extended or adjusted under 35 U.S.C. 154(b) by 745 days.

(21) Appl. No.: 17/432,001

(22) PCT Filed: Feb. 18, 2020

(86) PCT No.: PCT/EP2020/054150
§ 371 (c)(1),
(2) Date: Aug. 18, 2021

(87) PCT Pub. No.: WO2020/169551
PCT Pub. Date: Aug. 27, 2020

(65) Prior Publication Data
US 2022/0135943 A1    May 5, 2022

(30) Foreign Application Priority Data
Feb. 19, 2019    (EP) ..................... 19157908

(51) Int. Cl.
*C12N 5/071*    (2010.01)

(52) U.S. Cl.
CPC .......... *C12N 5/068* (2013.01); *C12N 2501/11* (2013.01); *C12N 2501/115* (2013.01); *C12N 2501/117* (2013.01); *C12N 2501/13* (2013.01); *C12N 2501/148* (2013.01); *C12N 2501/155* (2013.01); *C12N 2501/415* (2013.01); *C12N 2513/00* (2013.01); *C12N 2533/52* (2013.01); *C12N 2533/54* (2013.01); *C12N 2533/70* (2013.01)

(58) Field of Classification Search
CPC ................ C12N 5/068; C12N 2501/11; C12N 2501/115; C12N 2501/117; C12N 2501/13; C12N 2501/148; C12N 2501/155; C12N 2501/415; C12N 2513/00; C12N 2533/52; C12N 2533/54; C12N 2533/70
See application file for complete search history.

(56) References Cited

FOREIGN PATENT DOCUMENTS

| EP | 0218065 A2 | 4/1987 |
|---|---|---|
| EP | 3927812 B1 | 9/2023 |
| WO | 2010090513 A2 | 8/2010 |
| WO | 2014131033 A1 | 8/2014 |
| WO | 2017220586 A1 | 12/2018 |
| WO | 2018218344 A1 | 12/2018 |

OTHER PUBLICATIONS

Arora, M., "Cell Culture Media: A Review," Mater. Methods. 2013;3:175. doi.org/10.13070/mm.en.3.175. (Year: 2013).*
Corning® Matrigel® Matrix Frequently Asked Questions (FAQs) (2017-2019) (Year: 2017).*
European U.S. Appl. No. 19/157,908, Decision to Grant dated Oct. 8, 2023, 2 pages.
European U.S. Appl. No. 19/157,908, European Search Report dated Jul. 11, 2019, 5 pages.
Barker et al., "Lgr5+ve Stem Cells Drive Self-Renewal in the Stomach and Build Long-Lived Gastric Units In Vitro", Cell Stem Cell, vol. 6, Issue 1, 2010, pp. 25-36.
Sato et al., "Long-Term Expansion of Epithelial Organoids from Human Colon, Adenoma, Adenocarcinoma, and Barrett's Epithelium", Gastroenterology, 141(5), 2011, pp. 1762-1772.
Mahe et al., "Establishment of Gastrointestinal Epithelial Organoids", Current Protocols in Mouse Biology, 3(4), 2014, pp. 217-240.
Gjorevski et al., Nature, vol. 539, 2016, pp. 560-564.
Dimarco et al., Biomaterials Science, vol. 3, 2015, pp. 1376-1385.
Ricci-Vitiani et al. "Identification and Expansion of Human Colon-Cancer-Initiating Cells", Nature, 445, 2007, pp. 111-115.
Sato et al., Nature, vol. 459, 2009, pp. 262-265.

(Continued)

*Primary Examiner* — Tracy Vivlemore
*Assistant Examiner* — Eric J Rogers
(74) *Attorney, Agent, or Firm* — Kilpatrick Townsend & Stockton LLP

(57) ABSTRACT

The present invention provides a cell culture for obtaining an epithelial organoid, the cell culture comprising i) epithelial stem cells, or tissue fragments comprising said epithelial stem cells, ii) a basal medium for animal or human cells, iii) a Bone Morphogenetic Protein (BMP) inhibitor, iv) a mitogenic growth factor selected from the group consisting of epidermal growth factor (EGF), transforming growth factor-alpha (TGF-alpha), basic fibroblast growth factor (bFGF), brain-derived neurotrophic factor (BDNF) and keratinocyte growth factor (KGF), v) at least one soluble culture enhancer, wherein said at least one culture enhancer induces correct polarization of the cells in said cell culture within the developing organoid such as a laminin/entactin complex or entactin, and vi) a Wnt agonist if said epithelial stem cells, or tissue fragments comprising said epithelial stem cells are healthy cells, wherein said at least one soluble culture enhancer in said cell culture is a laminin/entactin complex in a concentration between 0.2 mg/ml and 3.4 mg/ml. A cell culture medium, an in-vitro method for obtaining an epithelial organoid, and an epithelial organoid obtained by said method are also disclosed.

9 Claims, 7 Drawing Sheets

(56) References Cited

OTHER PUBLICATIONS

Dimarco et al., "Protein-engineered scaffolds for in vitro 3D culture of primary adult intestinal organoids,"Biomaterials Science, vol. 3, 2015, pp. 1376-1385.
Gjorevski et al., "Designermatricesforintestinal stem cell and organoid culture," Nature, vol. 539, 2016, pp. 560-564.
Mahe et al., "Establishment of Gastrointestinal Epithelial Organoids", Current Protocols in Mouse Biology, vol. 3, 2013, pp. 217-240.
Barker et al., "$Lgr5^{+ve}$ Stem Cells Drive Self-Renewalin the Stomach and BuildLong-Lived Gastic Units In Vitro," Cell Stem Cell, vol. 6, 2010, pp. 25-36.
Ricci-Vitiani et al., "Identification and expansion of human colon-cancer-initiating cells," Nature, vol. 445, 2007, pp. 111-115.
Sato et al., "Long-term Expansion of Epithelial OrganoidsFrom Human Colon, Adenoma, Adenocarcinoma, andBarrett'sEpithelium," Gastroenterology, vol. 141, 2011, pp. 1762-1772.
Sato et al., "Single Lgr5 stem cells build crypt-villus structures in vitro without a mesenchymal niche," Nature, vol. 459, 2009, pp. 262.
InternationalPatent Application No. PCT/EP2020/054150, Written Opinion of the International Searching Authority, Mar. 16, 2020, 6 pages.

\* cited by examiner

CELL CULTURE MEDIUM AND METHOD FOR GENERATION OF EPITHELIAL ORGANOIDS FROM EPITHELIAL STEM CELLS

REFERENCE TO RELATED APPLICATION

This is the U.S. National Stage of international patent application PCT/EP2020/054150 (pending), filed on Feb. 18, 2020, and published on Aug. 27, 2020 with publication number WO 2020/169551. The PCT application claims the priority benefit of EP patent application Ser. No. 19/157,908.5, filed Feb. 19, 2019. The PCT application is hereby incorporated herein by reference its entirety for all purposes.

FIELD OF THE INVENTION

The invention generally relates to a cell culture, to a cell culture medium and a method for culturing epithelial stem cells for obtaining epithelial organoids. The invention particularly relates to the use of soluble culture enhancers within said cell cultures allowing to obtain said organoids without the need of a three-dimensional (3D) structure such as an extracellular matrix.

BACKGROUND OF THE INVENTION

In order to study the biology of tissues, development of diseases and perform pharmaceutical testing, in vitro models play a central role, especially in terms of potentially complementing or even replacing animal models. For epithelial tissues, three-dimensional (3D) culture methods have been described that rely on embedding cells in solid hydrogels functioning as extracellular matrices (ECMs) in order to grow so called 'epithelial organoids'. These 3D cultures resemble the cellular composition and architecture of parent epithelial tissues. Notably, the published protocols only allow for an expansion of the epithelial compartment. Another important feature is the cellular polarity which is resembled upon embedding in solid extracellular matrices or solid artificial ECM analogs.

The cellular polarity of cells plays an important structural as well as functional role, especially in many epithelial tissues. Growing these 'organoids' in solid ECMs leads to in vitro recapitulation of the epithelial tissue structure. However, since the 'organoids' need to be passaged and re-seeded and therefore recovered from the solid gels, these embedded cultures significantly hamper the convenient handling and more importantly automation of organoid cultivation. The same is true for downstream analysis or manipulation of organoids, since almost all handling steps require recovery from the solid gel. In addition, the embedding step causes a lack of reproducibility caused by a very heterogenous growth of the corresponding organoids.

On the other hand, 3D cultures grown in suspension have been described e.g. for neural or tumor stem cells (Ricci-Vitiani et al., 2007, Nature 445, 111-115). Such cultures allow expansion of stem cells as dense clusters of cells. However, they do not resemble tissue characteristics such as cellular heterogeneity and polarization of cells.

Epithelial organoids were first described by Sato et al. (2009, Nature 459, 262) for intestinal epithelial organoids based on the embedding single crypts or stem cells in a solid ECM or ECM-like hydrogel (Sato et al., 2009, Nature 459, 262) and was later adapted to further epithelial tissues (Barker et al., 2010, Cell stem cell 6, 25-36; Sato et al., 2011, Gastroenterology 141, 1762-1772). Cells or subunits of epithelial tissues are embedded in solidifying gels and later over-laid with medium containing mitogenic growth factors (e.g. EGF), BMP inhibitors (e.g. Noggin) and in the case of organoids from healthy tissues Wnt agonists. WO 2010/090513 A2 discloses a method for crypt-villus epithelial organoids, comprising a lumen, when isolated epithelial stem cells or tissue fragments are embedded in a natural or synthetic extracellular matrix and provided with a medium comprising said growth factors, inhibitors and agonists. As cells are grown in solid ECMs or ECM-derived gels, handling like passaging is significantly hampered. This method is well-described (Mahe, M. M., Aihara, E., Schumacher, M. A., Zavros, Y., Montrose, M. H., Helmrath, M. A., Sato, T., and Shroyer, N. F. (2013). Establishment of Gastrointestinal Epithelial Organoids. Current protocols in mouse biology 3, 217-240) and remained widely unmodified for epithelial organoids over the past few years. Notably, attempts have been made to replace widely undefined ECMs by so-called 'designer matrices' (Gjorevski et al., 2016, Nature 539, 560-564) or scaffolds (DiMarco et al., 2015, Biomaterials science 3, 1376-1385). Yet, both attempts suggested stiffness of the provided ECM to be key for the successful formation of epithelial organoids and cells or subunits of epithelial tissues have to be embedded to sufficiently provide such stiffness. So far, all attempts to culture epithelial organoids in suspension have failed. Currently, also a new culture method for intestinal epithelia, the MimEX™ system (R&D Systems, Inc., USA: Catalog Number MIM001) has been suggested. This method relies on the generation of 2D cultures on a feeder layer and subsequent transfer of these cultures to transwell inserts, which causes a transition to 3D-like cultures. Yet, this model only shows limited accessibility for handling and automation approaches.

Therefore, there is a need in the art for an improved or alternative cell culture or cell culture medium for the generation of epithelial organoids from epithelial stem cells, or tissue fragments comprising said epithelial stem cells and/or for methods for culturing epithelial stem cells, or tissue fragments comprising said epithelial stem cells for obtaining epithelial organoids.

SUMMARY OF THE INVENTION

So far, epithelial organoids can only be grown by embedding functional subunits of tissues or single stem cells into animal-derived or artificial extracellular matrices or matrix components that solidify and form a gel. Additionally, mitogenic growth factors (e.g. EGF), BMP inhibitors (e.g. Noggin) and in the case of organoids from healthy tissues Wnt agonists have to be provided in the culture medium. The culture medium is applied after solidification of the gel.

In contrast, we have directly resuspended and plated functional subunits or stem cells from human and murine epithelial tissues in said culture medium without embedding into solid ECMs. Additionally, we have added a soluble culture enhancer, which allowed the generation, expansion and cultivation of epithelial organoids in suspension cell cultures. Importantly, these soluble culture enhancers lead to correct basal-apical polarization and thus to successful growth of organoids in suspension, while in the absence of these soluble culture enhancers only depolarized spheres are formed that die within 2-4 days. Moreover, these cultures are characterized by enhanced expansion rates as compared to methods known in the art: epithelial organoids generated in the presence of culture enhancers and grown in suspension reach a size of approx. 400-650 µm after 3-4 days, whereas ECM-embedded epithelial organoids reach a comparable size only after 5-8 days.

Therefore, the cell culture as disclosed herein, the cell culture medium as disclosed herein and the methods as disclosed herein allow for the generation and propagation of epithelial organoids in cell cultures with the following benefits:

The soluble culture enhancers as disclosed herein do not significantly increase media viscosity The culture enhancers as disclosed herein induce the correct polarization of cells within the epithelial organoids, necessary for the generation and expansion of epithelial organoids and the formation of a lumen The cell cultures are characterized by enhanced growth rates as compared to methods used in the art.

It was surprising that certain extracellular matrix molecules or complexes of extracellular matrix molecules normally used for solidified 3D structures for generating epithelial organoids in cell culture media can induce in concentrations far below the solidification phase of the ECMs the correct polarization of cells within the epithelial organoids derived from epithelial stem cells. Therefore, the use of pre-solidified three-dimensional structures is not necessary when these molecules are used. Said molecules or complexes of molecules (herein referred to as soluble culture enhancers) that can induce said correct polarization are e.g. laminin/entactin (laminin/entactin complex) and a complex of molecules comprising in parts by weight about 60-85% laminin, 5-30% collagen IV, 1-10% heparan sulfate proteoglycan and 2-15% entactin (such a complex of proteins may be extracted as a protein extract e.g. from Engelbreth-Holm-Swarm (EHS) tumor or from human placenta or said complex of proteins may be artificially composed). Interestingly, not all molecules of extracellular matrix molecules normally used for solidified 3D structures can induce said correct polarization, and therefore are not suitable as culture enhancers as disclosed herein. Such molecules that do not induce the correct polarization are for example laminin (see Example 1), collagen or entactin as sole molecules (see Example 7). Further surprisingly it was found that the combination of two extracellular matrix molecules work as soluble culture enhancer as disclosed herein in the combination of laminin and entactin (laminin/entactin complex) but other combinations do not work such as laminin together with different collagens (see Example 7).

Therefore, it was completely unexpected that not any combination of ECM molecules and combinations of laminins and collagens in particular can induce correct polarization, as suggested by the abundance of those molecules in EHS tumor-derived ECMs, the consensus in the organoid field and different publications. Instead, successful organoid formation and polarization was dependent on the presence of at least laminin and entactin (as complex), whereas even both molecules alone were not sufficient.

Surprisingly, the generated epithelial organoids by the methods as disclosed herein are comparable to those generated in cell culture medium containing ECMs and using methods of the prior art with regard to morphological features and cellular composition. But the epithelial organoids developing in the cell culture medium and/or cell culture as disclosed herein show enhanced growth and facilitated handling/processing.

Therefore, the present invention comprises a cell culture for obtaining an epithelial organoid, a cell culture medium for culturing epithelial stem cells for obtaining an epithelial organoid, a method for obtaining an epithelial organoid, the use of soluble culture enhancers for obtaining an epithelial organoid, the epithelial organoid obtained by the methods disclosed herein, and the use of the epithelial organoid in a drug discovery screen or in regenerative medicine.

DETAILED DESCRIPTION OF THE INVENTION

Figure 1:
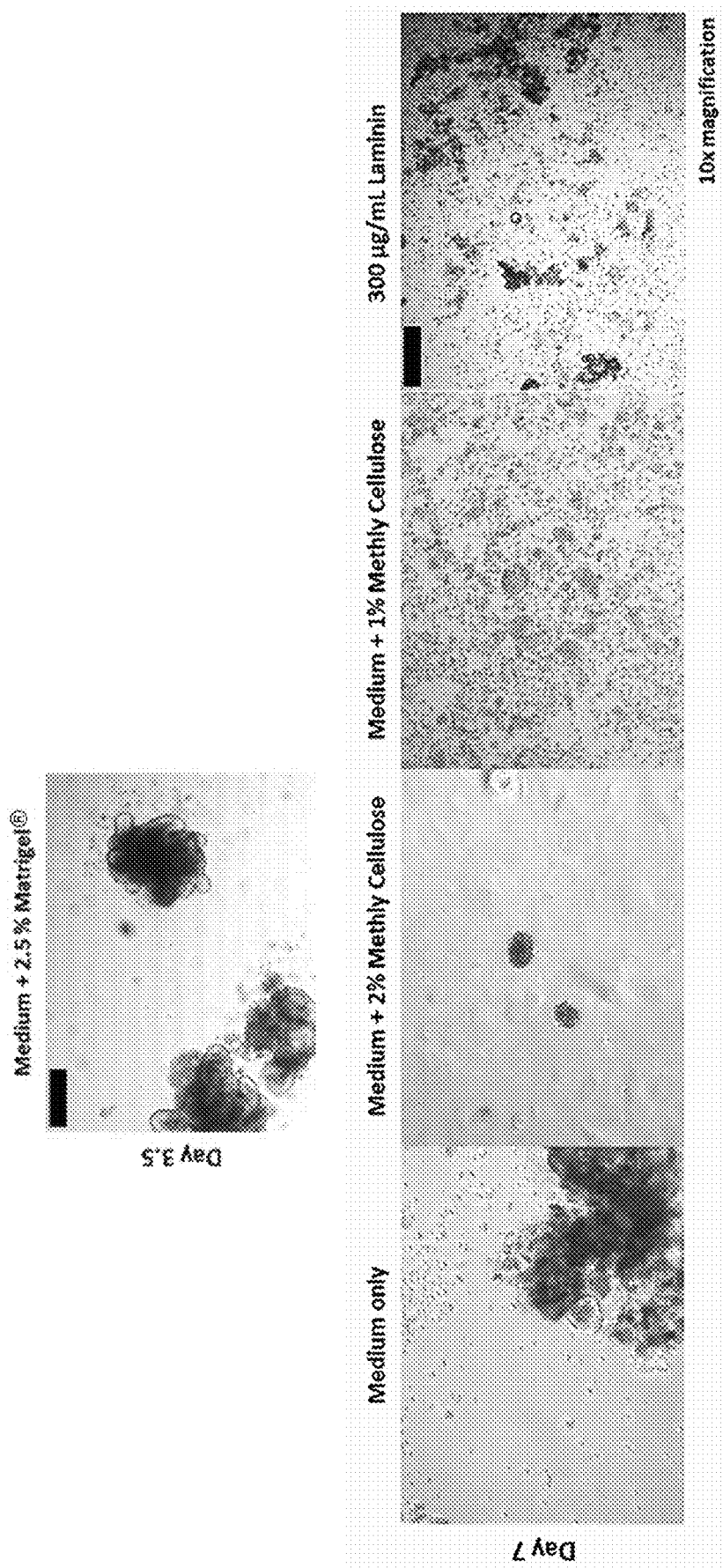
FIG. 1 shows that by cultivating small intestinal crypts in culture medium alone without embedding them in a solid ECM or ECM analogue does not yield intestinal organoids with crypt-villus domains. Additionally, culture medium with increased stiffness, e.g. by the addition of 2 or 1% methyl cellulose, also is not sufficient to generate typical crypt-villus organoids. Moreover, addition of 300 µg laminin (laminin derived from Engelbreth-Holm-Swarm murine sarcoma basement membrane: Merck, Cat. No. L2020-1 MG) was not sufficient to induce formation of correctly formed and polarized organoids. However, in the presence of a soluble culture enhancer, such as 2.5% matrix, crypt-villus organoids can successfully form. Additionally, these organoids already reach a size of approx. 400-650 µm diameter after 3.5 days and could already be passaged.

Up to now, it has been thought that in vitro development of epithelial organoids relies on the mechanical properties of the in vitro environment. Differentiation and expansion of stem cells has been described to be widely relying on the stiffness of the matrix. For intestinal and colonic epithelial organoids for example, a matrix stiffness of 1.3 kPa has been described as ideal for stem cell expansion and organoid formation, while 300 Pa only led to poor proliferation and formation of organoids that in most cases were depolarized. However, surprisingly we were able to identify soluble culture enhancers that allow for generation and maintenance of epithelial organoids in cell cultures, preferentially in suspension cell cultures. These organoids exhibit the correct cellular polarity and therefore also closely resemble many characteristics of epithelial tissues. It was absolutely surprising that not a certain stiffness of the cell culture medium is essential but the proper molecule(s), i.e. the soluble culture enhancer, induces the signaling to the cells for a correct polarization.

Accordingly, handling of such epithelial organoid is significantly facilitated as the developing organoid is in suspension. Moreover, this culture system paves the way for straight-forward automation of epithelial organoid cultivation and its broader application in pharmaceutical settings. More surprisingly, the corresponding epithelial organoids form much earlier upon seeding and show significantly enhanced proliferation rates.

In a first aspect the present invention provides a cell culture for obtaining an epithelial organoid, the cell culture comprising
  i) epithelial stem cells, or tissue fragments comprising said epithelial stem cells
  ii) a basal medium for animal or human cells,
  iii) a Bone Morphogenetic Protein (BMP) inhibitor,
  iv) a mitogenic growth factor selected from the group consisting of epidermal growth factor (EGF), transforming growth factor-alpha (TGF-alpha), basic fibroblast growth factor (bFGF), brain-derived neurotrophic factor (BDNF) and keratinocyte growth factor (KGF),
  v) at least one soluble culture enhancer, wherein said at least one culture enhancer induces correct polarization of the cells in said cell culture within the developing organoid, and
  vi) a Wnt agonist if said epithelial stem cells, or tissue fragments comprising said epithelial stem cells are healthy cells.

Said cell culture may be a suspension cell culture. Said cell culture, wherein said at least one soluble culture enhancer in said cell culture is a laminin/entactin complex. Said cell culture, wherein said at least one soluble culture enhancer in said cell culture is at least in a concentration of 0.2 mg/mL of said laminin/entactin complex.

Said cell culture, wherein said at least one soluble culture enhancer in said cell culture is in a concentration between 0.2 mg/mL and 3.4 mg/mL, 0.2 mg/mL and 3 mg/mL, 0.2 mg/mL and 2.5 mg/mL, 0.2 mg/mL and 2 mg/mL, 0.2 mg/mL and 1.5 mg/mL, or 0.2 mg/mL and 1 mg/mL of said laminin/entactin complex.

It is well-known in the art that a laminin/entactin complex solidifies to form a firm gel at about 3.5 mg/mL in a medium (Corning, Inc., USA, "Certificate of Analysis High Concentration Laminin/Entactin Complex", 2013, available from the Corning.com website). Therefore laminin/entactin remains fluidly in a medium below a concentration of 3.5 mg/mL. The concentration of 0.2 mg/mL of the laminin/entactin complex is sufficient to induce the correct polarization as shown in Example 2 and FIG. 2.

Said cell culture, wherein said at least one soluble culture enhancer is a complex of molecules (proteins) comprising in parts by weight about 60-85% laminin, 5-30% collagen IV, 1-10% heparan sulfate proteoglycan and 2-15% entactin. As entactin is a bridging molecule that interacts with laminin at least parts of laminin and entactin may exist in said complex of molecules as a laminin/entactin complex.

Said complex of molecules comprising in parts by weight about 60-85% laminin, 5-30% collagen IV, 1-10% heparan sulfate proteoglycan and 2-15% entactin, wherein in said cell culture said complex of molecules is at least in a concentration of 0.2 mg/mL. Said complex of molecules comprising in parts by weight about 60-85% laminin, 5-30% collagen IV, 1-10% heparan sulfate proteoglycan and 2-15% entactin, wherein in said cell culture said complex of molecules is at least in a concentration between 0.2 mg/ml and 3.2 mg/mL, 0.2 mg/mL and 3 mg/mL, 0.2 mg/mL and 2.5 mg/mL, 0.2 mg/mL and 2 mg/mL, 0.2 mg/mL and 1.5 mg/mL, or 0.2 mg/mL and 1 mg/mL.

Said complex of molecules comprising in parts by weight about 60-85% laminin, 5-30% collagen IV, 1-10% heparan sulfate proteoglycan and 2-15% entactin, wherein said complex may be derived from a protein extract of EHS tumor or human placenta. Said complex of molecules comprising in parts by weight about 60-85% laminin, 5-30% collagen IV, 1-10% heparan sulfate proteoglycan and 2-15% entactin, wherein said complex may be a protein extract of EHS tumor or human placenta. Extraction methods that result in said complex of molecules comprising in parts by weight about 60-85% laminin, 5-30% collagen IV, 1-10% heparan sulfate proteoglycan and 2-15% entactin, wherein said complex may be a protein extract of EHS tumor or human placenta are well-known in the art and are disclosed e.g. in U.S. Pat. No. 482,900.

Said complex of molecules comprising in parts by weight about 60-85% laminin, 5-30% collagen IV, 1-10% heparan sulfate proteoglycan and 2-15% entactin, wherein said complex may be provided as a composition of the single proteins of laminin, collagen IV, heparan sulfate proteoglycan and entactin by adding said single proteins, e.g. by using a source of commercially available single proteins, into said cell culture.

It is well-known in the art that a complex of Engelbreth-Holm-Swarm (EHS) tumor derived molecules, e.g. Matrigel® (Corning) solidifies at about 3.4 mg/mL in a medium (Corning, Inc., USA, SPC-356231 Rev 6.0 "Guidelines for Use" and "FAQ", available on the Corning.com website. Therefore said complex of Engelbreth-Holm-Swarm (EHS) tumor derived molecules remains fluidly in a medium below a concentration of 3.4 mg/mL. The concentration of 0.2 mg/mL of the complex of Engelbreth-Holm-Swarm (EHS) tumor derived molecules is sufficient to induce the correct polarization as shown in Example 1 and FIG. 1.

Said cell culture as disclosed herein, wherein said cell culture has a viscosity equal to or lower than 1 Pa*s at a shear rate of 1-100 Hz. Said cell culture as disclosed herein, wherein said cell culture has a viscosity equal to or lower than 1 Pas at a shear rate of 1-100 Hz, wherein the lowest concentration of the soluble culture enhancer in said cell culture is at least in a concentration of 0.2 mg/ml of said laminin/entactin complex or 0.2 mg/mL of said complex of molecules comprising in parts by weight about 60-85% laminin, 5-30% collagen IV, 1-10% heparan sulfate proteoglycan and 2-15% entactin.

Said cell culture, wherein said cell culture does not include or contain a pre-solidified 3D structure such as an ECM such as Matrigel® (Corning).

The laminin/entactin complex may be extracted from appropriate animal tissue by methods well known in the art or laminin/entactin complex commercially available may be used (e.g. Corning, Product No. 354359). The entactin may be extracted from appropriate animal tissue by methods well known in the art or entactin commercially available may be used (e.g. R&D systems, Cat. No. 2570-ND-050).

Preferentially, said complex of molecules comprising in parts by weight about 60-85% laminin, 5-30% collagen IV, 1-10% heparan sulfate proteoglycan and 2-15% entactin may be a protein extract of EHS tumor.

The complex of Engelbreth-Holm-Swarm (EHS) tumor derived molecules, wherein said complex of EHS tumor derived molecules comprises in parts by weight about 60-85% laminin, 5-30% collagen IV, 1-10% nidogen, 1-10% heparan sulfate proteoglycan and 1-5% entactin may be extracted from appropriate animal tissue by methods well known in the art (see e.g. U.S. Pat. No. 4,829,000) or such a complex commercially available may be used. Such a commercially available complex of Engelbreth-Holm-Swarm (EHS) tumor derived molecules is e.g. Matrigel® (Corning), Cultrex® Reduced Growth Factor Basement Membrane Matrix (Trevigen), Stem Cell Qualified ECM Gel (Merck) or Geltrex™ LDEV-Free Reduced Growth Factor Basement Membrane Matrix (ThermoFisher Scientific).

Said tissue fragments comprising said epithelial stem cells may be for example isolated colon crypts or small intestinal crypts. Said epithelial stem cells or said tissue fragments comprising said epithelial stem cells may be human or murine cells.

Basal media for animal or human cells are well-known in the art. Said basal medium for animal or human cells may be any cell culture medium containing amino acids, vitamins, inorganic salts, buffers, antioxidants and energy sources such as DMEM, advanced DMEM/F12, F12, or RPMI 1640.

Bone Morphogenetic Protein (BMP) inhibitors and used concentrations thereof in a cell culture or a cell culture medium for obtaining an organoid are well-known in the art as disclosed e.g. in WO 2010/090513 A2. Said Bone Morphogenetic Protein (BMP) inhibitor may be selected from the group consisting of Noggin, DAN, and DAN like proteins including Cerberus and Gremlin. The concentration of said Bone Morphogenetic Protein (BMP) inhibitors in cell cultures and/or cell culture medium may be at least 10 ng/ml, at least 20 ng/mL, at least 50 ng/mL or at least 100 ng/mL. The most preferred concentration may be 100 ng/mL.

Mitogenic growth factors and used concentrations thereof in a cell culture or a cell culture medium for obtaining an organoid are well-known in the art as disclosed e.g. in WO 2010/090513 A2.

Said mitogenic growth factor may be selected from the group consisting of epidermal growth factor (EGF), transforming growth factor-alpha (TGF-alpha), basic fibroblast growth factor (bFGF), brain-derived neurotrophic factor (BDNF) and keratinocyte growth factor (KGF). The concentrations of said mitogenic growth factors may be between 5 and 500 ng/mL, preferentially between 50 and 100 ng/ml.

Wnt agonists and used concentrations thereof in a cell culture or a cell culture medium for obtaining an organoid are well-known in the art as disclosed e.g. in WO 2010/090513 A2. Said Wnt agonist may be selected from the group consisting of Wnt family member, R-spondin family, Norrin, and an GSK-inhibitor. The Wnt family member includes Wnt-1/Int-1: Wnt-2/Irp (Int-1-related Protein): Wnt-2b/13; Wnt-3/Int-4; Wnt-3a: Wnt-4: Wnt-5a: Wnt-5b: Wnt-6: Wnt-7a: Wnt-7b: Wnt-8a/8d: Wnt-8b: Wnt-9a/14: Wnt-9b/14b/15: Wnt-10a; Wnt-10b/12; Wnt-11; and Wnt-16.

The R-spondin family comprises R-spondin-1, R-spondin-2, R-spondin-3, and R-spondin-4. Known GSK-inhibitors comprise small-interfering RNAs (siRNA), lithium, kenpaullone, SB 216763 and SB 415286 (Sigma-Aldrich), and FRAT-family members and FRAT-derived peptides that prevent interaction of GSK-3 with axin.

In another aspect, the present invention provides a cell culture medium for culturing epithelial stem cells, or tissue fragments comprising said epithelial stem cells, for obtaining an epithelial organoid, said cell culture medium comprising
i) a basal medium for animal or human cells,
ii) a Bone Morphogenetic Protein (BMP) inhibitor,
iii) a mitogenic growth factor selected from the group consisting of epidermal growth factor (EGF), transforming growth factor-alpha (TGF-alpha), basic fibroblast growth factor (bFGF), brain-derived neurotrophic factor (BDNF) and keratinocyte growth factor (KGF),
iv) at least one soluble culture enhancer, wherein said at least one culture enhancer induces correct polarization of the cells in said cell culture within the developing organoid, and
v) a Wnt agonist if said epithelial stem cells, or tissue fragments comprising said epithelial stem cells are healthy cells.

Said cell culture medium, wherein said at least one soluble culture enhancer in said cell culture medium is a laminin/entactin complex. Said cell culture medium, wherein said at least one soluble culture enhancer in said cell culture medium is at least in a concentration of 0.2 mg/mL of said laminin/entactin complex. Said cell culture medium, wherein said at least one soluble culture enhancer in said cell culture medium is in a concentration between 0.2 mg/mL and 3.4 mg/mL, 0.2 mg/mL and 3 mg/mL, 0.2 mg/mL and 2.5 mg/mL, 0.2 mg/mL and 2 mg/mL, 0.2 mg/mL and 1.5 mg/mL, or 0.2 mg/mL and 1 mg/mL of said laminin/entactin complex.

Said cell culture medium, wherein said at least one soluble culture enhancer is a complex of molecules (proteins) comprising in parts by weight about 60-85% laminin, 5-30% collagen IV, 1-10% heparan sulfate proteoglycan and 2-15% entactin.

Said complex of molecules comprising in parts by weight about 60-85% laminin, 5-30% collagen IV, 1-10% heparan sulfate proteoglycan and 2-15% entactin, wherein in said cell culture medium said complex of molecules is at least in a concentration of 0.2 mg/mL. Said complex of molecules comprising in parts by weight about 60-85% laminin, 5-30% collagen IV, 1-10% heparan sulfate proteoglycan and 2-15% entactin., wherein in said cell culture medium said complex of molecules is at least in a concentration between 0.2 mg/ml and 3.2 mg/mL, 0.2 mg/mL and 3 mg/mL, 0.2 mg/mL and 2.5 mg/mL, 0.2 mg/mL and 2 mg/mL, 0.2 mg/mL and 1.5 mg/mL, or 0.2 mg/mL and 1 mg/mL.

In a further aspect, the present invention provides an in-vitro method for culturing epithelial stem cells, or tissue fragments comprising said epithelial stem cells (in suspension), the method comprising culturing the epithelial stem cells, or tissue fragments comprising said epithelial stem cells, in a cell culture medium in the presence of (or comprising)
  i) a basal medium for animal or human cells
  ii) a Bone Morphogenetic Protein (BMP) inhibitor;
  iii) a mitogenic growth factor selected from the group consisting of epidermal growth factor (EGF), transforming growth factor-alpha (TGF-alpha), basic fibroblast growth factor (bFGF), brain-derived neurotrophic factor (BDNF) and keratinocyte growth factor (KGF),
  iv) at least one soluble culture enhancer, wherein said at least one culture enhancer induces correct polarization of the cells in said cell culture within the developing organoid, and
  v) a Wnt agonist if said epithelial stem cells, or tissue fragments comprising said epithelial stem cells are healthy cells.

In another aspect, the present invention provides an in vitro method for obtaining an epithelial organoid, the method comprising culturing epithelial stem cells, or tissue fragments comprising said epithelial stem cells in a cell culture medium (in suspension) in the presence of (comprising)
  i) a basal medium for animal or human cells
  ii) a Bone Morphogenetic Protein (BMP) inhibitor;
  iii) a mitogenic growth factor selected from the group consisting of epidermal growth factor (EGF), transforming growth factor-alpha (TGF-alpha), basic fibroblast growth factor (bFGF), brain-derived neurotrophic factor (BDNF) and keratinocyte growth factor (KGF),
  iv) at least one soluble culture enhancer, wherein said at least one culture enhancer induces correct polarization of the cells in said cell culture within the developing organoid, and
  v) a Wnt agonist if said epithelial stem cells, or tissue fragments comprising said epithelial stem cells are healthy cells.

Said methods, wherein said at least one soluble culture enhancer in said cell culture medium is a laminin/entactin complex. Said methods, wherein said at least one soluble culture enhancer in said cell culture medium is at least in a concentration of 0.2 mg/ml of said laminin/entactin complex. Said methods, wherein said at least one soluble culture enhancer in said cell culture medium is in a concentration between 0.2 mg/mL and 3.4 mg/mL, 0.2 mg/mL and 3 mg/mL, 0.2 mg/mL and 2.5 mg/mL, 0.2 mg/mL and 2 mg/mL, 0.2 mg/mL and 1.5 mg/mL, or 0.2 mg/mL and 1 mg/mL of said laminin/entactin complex.

Said methods, wherein said at least one soluble culture enhancer is a complex of molecules (proteins) comprising in parts by weight about 60-85% laminin, 5-30% collagen IV, 1-10% heparan sulfate proteoglycan and 2-15% entactin. Said complex of molecules comprising in parts by weight about 60-85% laminin, 5-30% collagen IV, 1-10% heparan sulfate proteoglycan and 2-15% entactin, wherein in said cell culture medium said complex of molecules is at least in a concentration of 0.2 mg/mL. Said complex of molecules comprising in parts by weight about 60-85% laminin, 5-30% collagen IV, 1-10% heparan sulfate proteoglycan and 2-15% entactin., wherein in said cell culture medium said complex of molecules is at least in a concentration between 0.2 mg/mL and 3.2 mg/mL, 0.2 mg/mL and 3 mg/mL, 0.2 mg/mL and 2.5 mg/mL, 0.2 mg/mL and 2 mg/mL, 0.2 mg/mL and 1.5 mg/mL, or 0.2 mg/mL and 1 mg/mL.

Said methods, wherein said method does not comprise a step of providing a pre-solidified three-dimensional (3-D) structure to said cell culture medium.

Said methods, wherein the method comprises the step of passaging the cells in said cell culture medium, and wherein said passaging is performed in an automated manner such as passaging or targeted seeding of the organoids by a liquid handling robot or an alternative automated cell culture system.

In another aspect the present invention provides the use of a soluble laminin/entactin complex or a soluble complex of molecules comprising in parts by weight about 60-85% laminin, 5-30% collagen IV, 1-10% heparan sulfate proteoglycan and 2-15% entactin as a soluble culture enhancer in a (suspension) cell culture or a cell culture medium for obtaining an epithelial organoid derived from epithelial stem cells, or tissue fragments comprising said epithelial stem cells. As said culture enhancers are in soluble form in said suspension cell culture or said cell culture medium this avoids a solidification of the suspension cell culture or the cell culture medium.

In a further aspect, the present invention provides an epithelial organoid, wherein said epithelial organoid is obtainable by the methods as disclosed herein. Said epithelial organoid, wherein said organoid grows from epithelial stem cells, or tissue fragments comprising said epithelial stem cells to a size of about 400-650 µm after 3 to 4 days. ECM-embedded epithelial organoids as disclosed e.g. in WO 2010/090513 A2 reach a comparable size only after 5-8 days.

The epithelial organoid as obtainable by the methods as disclosed herein, wherein said epithelial organoid reaches a size of about 400-650 µm in 90%, 80%, 70%, 60%, or 50% of the time compared to epithelial organoids that are developed without said soluble culture enhancers but in the presence of a 3D structure such as ECM. It is self-explaining that the epithelial organoid developed by the methods of the present invention has a biochemical distinction to the epithelial organoids developed by the methods of the prior art that need the presence of an ECM such as disclosed in WO 2010/090513 A2. This is e.g. indicative by the faster growing rate of the cells of the epithelial organoid as disclosed and/or the missing of a contact area between the cells of the organoid as disclosed herein and an ECM.

The epithelial organoid obtained by the methods as disclosed herein may have one of the following arrangements: The epithelial organoid may be a three-dimensional organoid, comprising crypt-like domains surrounding a central lumen lined by villus-like epithelial domains and filled with apoptotic cell bodies or a cyst-like structure, with cell layers surrounding a central lumen and filled with apoptotic cell. If organoids are derived from neoplastic tissues, they may be a three-dimensional structure of said crypt-villus- or cyst-like appearance or spheroid-like structures of round or irregular shape, lacking a central lumen. Further, said epithelial organoids contain stem or stem-like cells that can actively divide and give rise to all major differentiated cell lineages present in the parent epithelial structures. The cells within organoids derived from healthy tissues are polarized, as for example indicated by unequal expression of certain surface molecules on the apical and basal side. Cells within epithelial organoids derived from neoplastic tissue may show said polarization or may consist of unpolarized cells. Further, the epithelial organoid may be a three-dimensional organoid, comprising said structures, which are epithelial domains comprising differentiated cell types, and wherein non-epithelial cells are absent from said organoid.

In a further aspect the present invention provides the use of an epithelial organoid as disclosed herein in a drug discovery screen or in regenerative medicine.

For high-throughput purposes (e.g. for drug discovery screen), said epithelial organoids are cultured in multi-well plates such as, for example, 96 well plates or 384 well plates. Libraries of molecules are used to identify a molecule that affects said organoids. The cells are preferably exposed to multiple concentrations of a test agent for certain period of time. At the end of the exposure period, the cultures are evaluated. The term "affecting" is used to cover any change in a cell, including, but not limited to, a reduction in, or loss of, proliferation, a morphological change, and cell death. Said organoids can also be used to identify drugs that specifically target epithelial carcinoma cells, but not said organoids derived from healthy tissues. Cultures comprising organoids are useful in regenerative medicine, for example in post-radiation and/or post-surgery repair of the intestinal epithelium, in the repair of the intestinal epithelium in patients suffering from inflammatory bowel disease such as Crohn's disease and ulcerative colitis, and in the repair of the intestinal epithelium in patients suffering from short bowel syndrome.

All definitions, characteristics and embodiments defined herein with regard to the first aspect of the invention as disclosed herein also apply mutatis mutandis in the context of the other aspects of the invention as disclosed herein.

In addition to above described applications and embodiments of the invention further embodiments of the invention are described in the following without intention to be limited to these embodiments.

EMBODIMENTS

In an embodiment of the invention a suspension cell culture for obtaining an epithelial organoid is generated. The suspension culture may comprise
i) healthy epithelial stem cells, or tissue fragments comprising said epithelial stem cells
i) a basal medium for animal or human cells, e.g. advanced DMEM/F12
ii) a Bone Morphogenetic Protein (BMP) inhibitor, e.g. Noggin
iii) a mitogenic growth factor, e.g. EGF
iv) a soluble culture enhancer that induces correct polarization of the cells as disclosed herein, e.g. laminin/entactin in a concentration of 0.3 mg/mL, and
v) a Wnt agonist, e.g. R-spondin 1 and/or Wnt-3
The suspension culture develops within 2-4 days an organoid that is floating the cell culture. The generated epithelial organoid may be used e.g. for analyzing the biology of healthy epithelial tissues, drug toxicity screening or their application in regenerative medicine.

In an embodiment of the invention a suspension cell culture for obtaining an organoid is generated. The suspension culture may comprise
i) epithelial stem cells from a diseased tissue, e.g. inflammatory bowel disease or Crohn's disease, or tissue fragments comprising said epithelial stem cells
i) a basal medium for animal or human cells, e.g. advanced DMEM/F12
ii) a Bone Morphogenetic Protein (BMP) inhibitor, e.g. Noggin
iii) a mitogenic growth factor, e.g. EGF
iv) a soluble culture enhancer that induces correct polarization of the cells as disclosed herein, e.g. laminin/entactin in a concentration of 0.3 mg/mL, and
v) a Wnt agonist, e.g. R-spondin 1 and/or Wnt-3.
The suspension culture develops within 2-4 days organoids that are floating in the cell culture. The generated organoids may be used e.g. for analyzing the biology of diseased epithelial tissues or drug screening.

In an embodiment of the invention a suspension cell culture for obtaining an organoid is generated. The suspension culture may comprise
i) adenoma or carcinoma epithelial stem cells, or tissue fragments comprising said adenoma or carcinoma epithelial stem cells
i) a basal medium for animal or human cells, e.g. advanced DMEM/F12
ii) a Bone Morphogenetic Protein (BMP) inhibitor, e.g. Noggin
iii) a mitogenic growth factor, e.g. EGF
iv) a soluble culture enhancer that induces correct polarization of the cells as disclosed herein, e.g. laminin/entactin in a concentration of 0.3 mg/mL.
The suspension culture develops within 2-4 days organoids that are floating in the cell culture. The generated organoid may be used e.g. for analyzing the biology of neoplastic epithelial tissues, drug screening or the generation of animal disease models.

In another embodiment of the invention a cell culture medium for culturing epithelial stem cells, or tissue fragments comprising said epithelial stem cells, for obtaining an epithelial organoid, is generated. Said cell culture medium may comprise
i) a basal medium for animal or human cells, e.g. advanced DMEM/F12
ii) a Bone Morphogenetic Protein (BMP) inhibitor, e.g. Noggin
iii) a mitogenic growth factor, e.g. EGF
iv) a soluble culture enhancer that induces correct polarization of the cells as disclosed herein, e.g. laminin/entactin in a concentration of 0.3 mg/mL
v) a Wnt agonist, e.g. R-spondin 1 and/or Wnt-3 if said epithelial stem cells, or tissue fragments comprising said epithelial stem cells are healthy cells.

After addition of epithelial stem cells, or tissue fragments comprising said epithelial stem cells epithelial organoids may be developed within 2-4 days. This cell culture medium may be without an ECM or may comprise temporary during culturing an ECM or may have constantly during culturing an ECM although the organoid would grow also without the ECM.

In a further embodiment of the invention epithelial stem cells, or tissue fragments comprising said epithelial stem cells, are cultured in the presence of i) a cell culture medium without an ECM, comprising a basal medium for animal or human cells, e.g. advanced DMEM/F12
ii) a Bone Morphogenetic Protein (BMP) inhibitor, e.g. Noggin
iii) a mitogenic growth factor, e.g. EGF
iv) a soluble culture enhancer that induces correct polarization of the cells as disclosed herein, e.g. laminin/entactin in a concentration of 0.3 mg/mL
v) a Wnt agonist, e.g. R-spondin 1 and/or Wnt-3 if said epithelial stem cells, or tissue fragments comprising said epithelial stem cells are healthy cells.

After addition of epithelial stem cells, or tissue fragments comprising said epithelial stem cells epithelial organoids may be developed within 2-4 days. The culturing of said cells in said culture medium may comprise the passaging of cells, e.g. after 3 days. In a variant of this embodiment the passaging of cells is performed in an automated process, e.g. by using a liquid handling robot or alternative automated cell culture system for passaging or targeted seeding of the organoids.

In an embodiment of the invention a soluble culture enhancer, e.g. laminin/entactin is used in a suspension cell culture or a cell culture medium for obtaining an epithelial organoid derived from epithelial stem cells, or tissue fragments comprising said epithelial stem cells. The use of soluble laminin/entactin allows the absence of an ECM for generating an epithelial organoid derived from epithelial stem cells, or tissue fragments comprising said epithelial stem cells.

In a further embodiment of the invention an epithelial organoid is obtained by the methods as disclosed herein. This epithelial organoid may be used e.g. for analyzing the biology of healthy or neoplastic epithelial tissues, drug screening, regenerative medicine, or the generation of animal disease models.

Definitions

Unless defined otherwise, technical and scientific terms used herein have the same meaning as commonly understood by one of ordinary skill in the art to which this invention belongs.

As used herein the term "comprising" or "comprises" is used in reference to compositions, methods, and respective component(s) thereof, that are essential to the method or composition, yet open to the inclusion of unspecified elements, whether essential or not. The term "about" as used herein with respect to measured refers to a range around the number indicated. The term "about" may refer to plus or minus 10% of the indicated value. Many organs of adult humans and mice contain distinct stem cell populations. These adult stem cells may show varying, tissue-specific characteristics, yet they share certain characteristics that define them as stem cells. Essential characteristics are: self-renewal, capability to generate offspring able to differentiate into all (more specialized) lineages of the respective tissue and by this the capability to regenerate the tissue to a tissue-specific extent for example after injury. In order to keep said characteristics, stem cells reside in the respective stem cell niche, a specialized microenvironment within tissues providing all relevant signals.

Epithelial stem cells are capable of regenerating epithelia, including distinct specialized epithelial cell types. Epithelial stem cells may be cells which can give rise to epithelium no matter where they are derived, isolated or generated from, e.g. the may be derived or generated from iPS cells or transdifferentiated cells. As the functions and composition of epithelia varies in different organs, also the cell turnover and therefore proliferation rate of said epithelial stem cells is various. Well-known examples for epithelia with rapid turnover are skin and intestine, while pancreas and liver represent epithelia with slow turnover rates. The epithelial stem cell niches are located in specific subunits of the tissues, accordingly the protocols for the preparation of said stem cells varies between different tissues.

In the small and the large intestine, epithelial stem cells reside in crypts. Protocols for the isolation of crypts are known by one of ordinary skill in the art. The isolation can for example be done by incubation of rinsed colonic or intestinal tissue in chelating buffers such as EDTA or EGTA, in order to disrupt calcium- and magnesium-dependent cell-cell and cell-basement membrane bindings. After washing the tissue carefully with chelating agent-free buffer, crypts can be released by shearing off the crypts by vigorous pipetting. Larger tissue fragments can be removed using a 70 µm mesh strainer in order to obtain "purified" crypts. In order to obtain a single cell suspension (containing epithelial stem cells) the crypts can subsequently be incubated in diluted proteolytic enzymes, such as collagenase, dispase, trypsin or preferably papain. A subsequent filtration step can be used to remove remnant undigested tissue pieces. Similar methods can be used to isolate fragments and or cells from stomach, pancreas or salivary gland. In addition, commercial enzyme kits and methods can be used to obtain said cells.

Fragments or cells suitable for said generation of organoids from neoplastic epithelial tissues can be isolated by protocols known by one of ordinary skill in the art. For example, said tissues can be minced to pieces of 4-6 mm and incubated in diluted proteolytic enzymes such as dispase, trypsin, papain or preferably collagenase. Tissue fragments can be generated by subsequent shearing using vigorous pipetting. Removal of larger, undigested tissue pieces can be achieved by filtration using a 100 µm mesh strainer. In order to obtain a single cell suspension the tissue fragments can subsequently be incubated in diluted proteolytic enzymes, such as collagenase, dispase, trypsin or papain. A subsequent filtration step can be used to remove remnant undigested tissue pieces. In addition, commercial enzyme kits and methods can be used to obtain said cells.

Epithelial stem cells from or stem-like cells within said tissues can be isolated using methods known by one of ordinary skill in the art. A preferred method is based on the fact that certain surface molecules are expressed by said stem or stem-like cells in a specific manner, as known in the art. A preferred method is to prepare single cell suspension from said epithelial tissues by methods known in the art and contacting them with compounds binding said surface molecules, such as monoclonal antibodies. Said stem cell are then isolated by isolating said compound, for example by using magnetic beads or fluorescence activated cell sorting, as known by one of ordinary skill. Preferred compounds are monoclonal antibodies specifically binding Lgr5 and/or Lgr6 for intestinal or colonic epithelial stem cells or Lgr5 and/or CD133 for colorectal stem-like cells.

The term "tumor" is known medically as a neoplasm. Not all tumors are cancerous: benign tumors do not invade neighboring tissues and do not spread throughout the body. The term "cancer" is known medically as a malignant neoplasm. Cancer is a broad group of diseases involving unregulated cell growth. In cancer, cells (cancerous cells) divide and grow uncontrollably, forming malignant tumors, and invading nearby parts of the body. The cancer may also spread to more distant parts of the body through the lymphatic system or bloodstream. There are over 200 different known cancers that affect humans.

The term "adenoma" describes a benign tumor of epithelial tissue with glandular origin, glandular characteristics, or both. Adenomas can grow from many glandular organs, including the adrenal glands, pituitary gland, thyroid, prostate, and others. Some adenomas grow from epithelial tissue in non-glandular areas but express glandular tissue. Although adenomas are benign, over time they may transform to become malignant, at which point they are called adenocarcinomas.

The term "extracellular matrix" (ECM) as used herein refers to a collection of extracellular molecules secreted by connective tissue that provides structural and biochemical support to the surrounding cells (naturally occurring ECM) and/or refers to natural, semi-synthetic and synthetic biomaterials or mixtures thereof that can build matrices or scaffolds that mimic a cellular niche e.g. for stem cells during culturing them. All these structural supports, matrices and scaffolds have the inherent feature that cells such as epithelial stem cells, or tissue fragments comprising said epithelial stem cells can attach to these structures, i.e. to the ECM, and therefore said cells are not in suspension in a cell culture medium. A scaffold provides three dimensional networks or structures. Suitable synthetic materials for said scaffold comprise polymers selected from porous solids, nanofibers, and hydrogels such as, for example, peptides including self-assembling peptides, hydrogels composed of polyethylene glycol phosphate, polyethylene glycol fumarate, polyacrylamide, polyhydroxyethyl methacrylate, polycellulose acetate, and/or co-polymers thereof.

ECM is composed of a variety of polysaccharides, water, elastin, and glycoproteins, wherein the glycoproteins comprise collagen, entactin (nidogen), fibronectin, and laminin. ECM is secreted by connective tissue cells. Different types of ECM are known, comprising different compositions including different types of glycoproteins and/or different combination of glycoproteins. Said ECM can be provided by culturing ECM-producing cells, such as for example fibroblast cells, in a receptacle, prior to the removal of these cells and the addition of e.g. isolated crypts or epithelial stem cells. Examples of extracellular matrix-producing cells are chondrocytes, producing mainly collagen and proteoglycans, fibroblast cells, producing mainly type IV collagen, laminin, interstitial procollagens, and fibronectin, and colonic myofibroblasts producing mainly collagens (type I, III, and V), chondroitin sulfate proteoglycan, hyaluronic acid, fibronectin, and tenascin-C.

Alternatively, said ECM is commercially provided. Examples of commercially available extracellular matrices are extracellular matrix proteins (Invitrogen) and Matrigel® (Corning). Again, the ECM has a solidified structure that allows for attachment/adhesion of cells in culture.

The term "pre-solidified three-dimensional (3D) structure" in the context of providing or not providing said pre-solidified three-dimensional (3D) structure to a cell culture medium as disclosed means that a prefabricated 3D structure such as Matrigel® (Corning) is mixed with said cells and incubated at 37° C. to form a firm gel. Alternatively, a prefabricated 3D structure such as Matrigel® (Corning) is incubated at 37° C. to form a firm gel without cells. Those solid structures could be added to a cell culture medium, representing floating pre-solidified three-dimensional (3D) structures in a suspension culture.

Cell culture is the process by which cells are grown under controlled conditions, generally outside their natural environment. After the cells of interest have been isolated from living tissue, they can subsequently be maintained under carefully controlled conditions. These conditions vary for each cell type, but generally consist of a suitable vessel with a substrate or medium that supplies the essential nutrients (amino acids, carbohydrates, vitamins, minerals), growth factors, hormones, and gases ($CO_2$, $O_2$), and regulates the physio-chemical environment (pH buffer, osmotic pressure, temperature). Most cells require a surface or an artificial substrate (adherent or monolayer culture) whereas others can be grown free floating in culture medium (suspension culture). Therefore, the term "suspension (cell) culture" means that the cells or multicellular units of a culture grow free floating in the culture medium, i.e. they are in suspension. The key is that these cells or multicellular units are grown in a medium with a viscosity not significantly higher as compared to basal media for animal or human cells.

The term "basal medium for animal or human cells" as used herein refers to a defined synthetic medium for animal or human cells that is buffered preferably at a pH between 7.2 and 7.6, preferentially at about a pH of 7.4 with a carbonate-based buffer, while the cells are cultured in an atmosphere comprising between 5% and 10% $CO_2$, preferably about 5% $CO_2$. Basal media for animal or human cells are well-known in the art. A preferred basal medium suited for animal or human cells may be selected from DMEM/F12 and RPMI 1640 supplemented with glutamine, insulin, Penicillin/streptomycin and transferrin. In a further preferred embodiment, Advanced DMEM/F12 or Advanced RPMI is used, which is optimized for serum free culture and already includes insulin. In this case, said Advanced DMEM/F12 or Advanced RPMI medium is preferably supplemented with glutamine and Penicillin/streptomycin. It is furthermore preferred that said medium is supplemented with a purified, natural, semi-synthetic and/or synthetic growth factor and does not comprise an undefined component such as fetal bovine serum or fetal calf serum. Supplements such as, for example, B27, N-Acetylcysteine and N2 stimulate proliferation of some cells and can further be added to the medium, if required.

The term "cell culture medium" is synonymous with medium, culture medium or cell medium.

An organoid is a miniaturized and simplified version of an organ produced in vitro in three dimensions that shows realistic micro-anatomy. They are derived from one or a few cells from a tissue, embryonic stem cells or induced pluripotent stem cells, which can self-organize in three-dimensional culture owing to their self-renewal and differentiation capacities. Human embryonic stem cells can be isolated from embryos without destruction as disclosed e.g. in WO 03/046141. Epithelial organoids are derived from epithelial stem cells or tissue fragments comprising said epithelial stem cells. The epithelial organoids obtained by the methods as disclosed herein are artificial epithelial organoids, they are not in-vivo naturally grown organoids.

Bone morphogenetic proteins (BMPs) interact with specific receptors on the cell surface, referred to as bone morphogenetic protein receptors (BMPRs). Signal transduction through BMPRs results in mobilization of members of the SMAD family of proteins. The signaling pathways involving BMPs, BMPRs and SMADs are important in the development of several organs.

The term "Bone Morphogenetic Protein (BMP) inhibitor" is defined as an agent that binds to a BMP molecule to form a complex wherein the BMP activity is neutralized, for example by preventing or inhibiting the binding of the BMP molecule to a BMP receptor. Alternatively, the BMP inhibitor is an agent that acts as an antagonist or reverse agonist. This type of inhibitor binds with a BMP receptor and prevents binding of a BMP to said receptor. An example of a latter agent is an antibody that binds a BMP receptor and prevents binding of BMP to the antibody-bound receptor.

Several classes of natural BMP-binding proteins are known, including Noggin, Chordin and chordin-like proteins comprising chordin domains, Follistatin and follistatin-related proteins comprising a follistatin domain, DAN and DAN-like proteins comprising a DAN cysteine-knot domain, sclerostin/SOST, decorin, and alpha-2 macroglobulin. The preferred BMP inhibitor is Noggin. Noggin is preferably added to the cell culture medium at a concentration of at least 10 ng/mL, more preferred at least 20 ng/mL, more preferred at least 50 ng/mL, more preferred at least 100 ng/mL. A most preferred concentration is approximately 100 ng/mL or 100 ng/mL. During culturing of stem cells, said BMP inhibitor is preferably added to the culture medium every second day, while the culture medium is refreshed preferably every fourth day.

A mitogenic growth factor is a growth factor that triggers mitosis of a cell. The mitogenic growth factor may be selected from a family of growth factors comprising epidermal growth factor (EGF), Transforming Growth Factor-alpha (TGF-alpha), basic Fibroblast Growth Factor (bFGF), brain-derived neurotrophic factor (BDNF), and Keratinocyte Growth Factor (KGF).

A preferred mitogenic growth factor is EGF. EGF is preferably added to the basal culture medium at a concentration of between 5 and 500 ng/ml or of at least 5 and not higher than 500 ng/mL. A preferred concentration is at least 10, 20, 25, 30, 40, 45, or 50 ng/mL and not higher than 500, 450, 400, 350, 300, 250, 200, 150, or 100 ng/mL. A more preferred concentration is at least 50 and not higher than 100 ng/mL. An even more preferred concentration is 50 ng/mL. The same concentrations could be used for a FGF, preferably for FGF10 or FGF7. Also more than one mitogenic growth factor may be added to the culture medium.

During culturing of stem cells, said mitogenic growth factor is preferably added to the culture medium every second day, while the culture medium is refreshed preferably every fourth day.

The terms "soluble culture enhancer" or "culture enhancer" as used herein refer to a molecule or a complex of molecules in solution (in a cell culture medium or suspension cell culture) that allows for generation, expansion and cultivation of organoids in suspension cultures. The (soluble) culture enhancer does not form or contribute to a macroscopic solidified structure, matrix or scaffold to that cells of a cell culture might attach. Said 'culture enhancers' lead to correct basal-apical polarization and thus to successful growth of organoids in suspension cultures while in the absence of said soluble culture enhancers in ECM free media only depolarized spheres are formed that die within 2-4 days. The terms "soluble culture enhancers" and "culture enhancers" may be used interchangeably.

The culture enhancer may be a laminin/entactin complex or a complex of molecules comprising in parts by weight about 60-85% laminin, 5-30% collagen IV, 1-10% heparan sulfate proteoglycan and 2-15% entactin.

The terms "laminin/entactin complex" or "laminin/entactin" can be used interchangeably. Laminin and entactin are a components of basement membranes of cells. Entactin is a bridging molecule that interacts with laminin, both molecules are assembled intracellularly before they are secreted. A good source for extracting the laminin/entactin is e.g. Engelbreth-Holm-Swarm (EHS) mouse tumor. Methods for extracting the laminin/entactin complex are well-known in the art. The laminin/entactin is also commercially available, e.g. from Corning. Engelbreth-Holm-Swarm (EHS) tumor produces large amounts of basement membrane (BM) components, which are widely used as cell culture substrates mimicking BM functions. EHS tumor arose spontaneously in an ST/Eh strain mouse and has been propagated by transplantation.

The terms "complex of molecules comprising in parts by weight about 60-85% laminin, 5-30% collagen IV, 1-10% heparan sulfate proteoglycan and 2-15% entactin" and "complex of proteins comprising in parts by weight about 60-85% laminin, 5-30% collagen IV, 1-10% heparan sulfate proteoglycan and 2-15% entactin" can be used interchangeably.

The term "said complex of molecules comprising in parts by weight about 60-85% laminin, 5-30% collagen IV, 1-10% heparan sulfate proteoglycan and 2-15% entactin is derived from a protein extract of EHS tumor means an extract (or protein extract) of Engelbreth-Holm-Swarm (EHS) tumor derived molecules, wherein said extract (or protein extract) of EHS tumor derived molecules comprises in parts by weight about 60-85% laminin, 5-30% collagen IV, 1-10% heparan sulfate proteoglycan and 2-15% entactin". U.S. Pat. No. 482,900 discloses said composition of protein extracts: 60-85% laminin, 5-30% collagen IV, 1-10% nidogen, 1-10% heparan sulfate proteoglycan and 1-5% entactin. Later it was identified that nidogen is identical to entactin, therefore, herein the values have been added together to 2-15% entactin.

Matrigel® is a commercially available product from Corning. Matrigel® is a reconstituted basement membrane preparation that is extracted from the Engelbreth-Holm-Swarm (EHS) mouse sarcoma, a tumor rich in extracellular matrix proteins. This material, once isolated, is about 60% laminin, 30% collagen IV, and 8% entactin. Entactin is a bridging molecule that interacts with laminin and collagen IV, and contributes to the structural organization of these extracellular matrix molecules. Matrigel® also contains heparan sulfate proteoglycan and other molecules.

A method for extraction of said complex of molecules comprising in parts by weight about 60-85% laminin, 5-30% collagen IV, 1-10% heparan sulfate proteoglycan and 2-15% entactin may be performed e.g. as follows. First, Engelbreth-Holm-Swarm (EHS) tumor grown in mice is resected from animals in concordance with local ethics approvals. The tissue is homogenized in 20% NaCl (w/w) containing 4 mM EDTA, 2 mM NEM and 20 mM TRIS-HCl at pH 7.4. Said buffer is referred to as 20% NaCl buffer hereafter. In order to remove proteins originating from cells and serum, the homogenate is mixed thoroughly and centrifuged at 10000 g for 15 minutes. This procedure is repeated for two more times. Next, the residual material is extracted with 2 M urea in 50 mM Tris-HCl and 150 mM NaCl buffer at pH 7.4 by incubating it overnight at 4° C. and then centrifuged at 10000 g and 4° C. for at least 30 min. The supernatant can then be dialyzed against a suitable buffer such as phosphate-buffered saline (PBS) pH 7.4. In order to further remove any insoluble residuals, the dialyzed fraction can be centrifuged again at 10000 g and 4° C. for at least 30 min. This fraction contains said Engelbreth-Holm-Swarm (EHS) tumor derived molecules.

The soluble culture enhancers may be used in the suspension cell culture or the cell culture medium in the following concentrations: Between 0.2 mg/mL and 3.4 mg/mL, 0.2 mg/mL and 3 mg/mL, 0.2 mg/mL and 2.5 mg/mL, 0.2 mg/mL and 2 mg/mL, 0.2 mg/mL and 1.5 mg/mL, or 0.2 mg/mL and 1 mg/mL if said culture enhancer is the laminin/entactin complex. Between 0.2 mg/mL and 3.2 mg/mL, 0.2 mg/mL and 3 mg/mL, 0.2 mg/mL and 2.5 mg/mL, 0.2 mg/mL and 2 mg/mL, 0.2 mg/mL and 1.5 mg/mL, 0.2 mg/mL and 1 mg/mL, or 0.2 mg/mL and 0.5 mg/mL if said culture enhancer is a complex of molecules comprising in parts by weight about 60-85% laminin, 5-30% collagen IV, 1-10% heparan sulfate proteoglycan and 2-15% entactin.

The term "induces correct polarization of the cells in said (suspension) cell culture" in the context of a soluble culture enhancer in a cell medium for generating a epithelial organoid means that said culture enhancer triggers the formation of polarized cells expressing basement membrane-specific markers (such as EpCAM in intestinal organoids) on the interface of medium and cells, while apical markers (such as F-actin) are expressed on the luminal membrane of organoids developing a lumen in vitro. Notably, due to the nature of neoplastic cells, this polarization cannot necessarily be observed in organoids derived thereof. During culturing of epithelial stem cells, said soluble culture enhancer is preferably added to the culture medium every second day, while the culture medium is refreshed preferably every fourth day.

In the case of non-adenomas or non-carcinomas (i.e. healthy epithelial stem cells or isolated crypts) Wnt agonists have to be provided in the culture medium for the proliferation of the cells.

In the reverse conclusion if the organoid is based on adenoma (epithelial adenoma cell) and/or tumor cells of (colon or small intestinal) epithelial stem cells, then it is not necessary to provide a Wnt agonist in the suspension culture and/or cell culture medium as disclosed herein as these cells regularly have a mutation that activates the Wnt signaling of the cells, for example an Adenomatous polyposis coli (APC) mutation.

The term "said epithelial stem cells, or tissue fragments comprising said epithelial stem cells are healthy cells" means that the epithelial stem cells, or tissue fragments comprising said epithelial stem cells are normal cells or cells from an non-adenoma or non-carcinoma diseased tissue, such as inflammatory bowel disease or Crohn's Disease which show a disease state but are not neoplastic. In contrast thereto are abnormal cells that might be adenomas or tumor cells.

The term "diseased tissue" as used herein means cells and/or tissue that is not healthy but does not comprise neoplastic or cancerous cells. Examples for diseased tissues are inflammatory bowel disease or Crohn's Disease.

The Wnt signalling pathway is defined by a series of events that occur when a Wnt protein binds to a cell-surface receptor of a Frizzled receptor family member. This results in the activation of Disheveled family proteins which inhibit a complex of proteins that includes axin, GSK-3, and the protein APC to degrade intracellular β-catenin. The resulting enriched nuclear β-catenin enhances transcription by TCF/LEF family transcription factors.

A Wnt agonist is defined herein as an agent that activates TCF/LEF-mediated transcription in a cell. Wnt agonists are therefore selected from true Wnt agonists that bind and activate a Frizzled receptor family member including any and all of the Wnt family proteins, an inhibitor of intracellular β-catenin degradation, and activators of TCF/LEF. Said Wnt agonist may be selected from the group consisting of Wnt family member, R-spondin family, Norrin, and an GSK-inhibitor.

The Wnt family member includes Wnt-1/Int-1: Wnt-2/Irp (Int-1-related Protein); Wnt-2b/13; Wnt-3/Int-4: Wnt-3a: Wnt-4: Wnt-5a: Wnt-5b; Wnt-6; Wnt-7a: Wnt-7b: Wnt-8a/8d: Wnt-8b: Wnt-9a/14: Wnt-9b/14b/15: Wnt-10a: Wnt-10b/12: Wnt-11; and Wnt-16. The R-spondin family comprises R-spondin-1, R-spondin-2, R-spondin-3, and R-spondin-4. Known GSK-inhibitors comprise small-interfering RNAs (siRNA), lithium, kenpaullone, SB 216763 and SB 415286 (Sigma-Aldrich), and FRAT-family members and FRAT-derived peptides that prevent interaction of GSK-3 with axin.

In an embodiment of the invention, said Wnt agonist comprises or consists of R-spondin 1. R-spondin 1 may be preferably added to the cell culture medium at a concentration of at least 50 ng/mL, more preferred at least 100 ng/ml, more preferred at least 200 ng/ml, more preferred at least 300 ng/mL, more preferred at least 500 ng/mL. A most preferred concentration of R-spondin 1 is approximately 500 ng/ml or 500 ng/ml. During culturing of stem cells, said Wnt family member is preferably added to the cell culture medium every second day, while the culture medium is refreshed preferably every fourth day.

In another embodiment of the invention, a Wnt agonist is selected from the group consisting of: R-spondin, Wnt-3a and Wnt-6. More preferably, R-spondin and Wnt-3a are both used as Wnt agonist. Preferred concentrations may be approximately 500 ng/ml or 500 ng/mL for R-spondin and approximately 100 ng/ml or 100 ng/ml for Wnt3a.

EXAMPLES

Example 1: Culture Enhancers Allow for Formation of Organoids Independent of Media Viscosity In order to grow small intestinal organoids from small intestinal crypts, the crypts were harvested from the small intestine from C57B16 mice according to published procedures. In brief, after dissecting the small intestine, it was flushed with buffer, longitudinally opened and cut into pieces of approx. 4 mm and incubated in D-PBS containing 7 mM EDTA for 30 minutes on ice. Next, the crypts were released by repeated pipetting and harvested by letting remnant tissue pieces settle down by gravity and harvesting the supernatant containing crypts and some villi. The villi were removed by filtration though a SmartStrainer® brand cell strainer (Miltenyi Biotec) of 70 µm mesh size. The isolated crypts were centrifuged, resuspended in small intestinal organoid medium and seeded in ultra-low attachment plates.

To test the capability of supporting organoid formation and growth, different supplements were added. Crypts incubated without further supplements or in medium containing 1-2% methyl cellulose or 300 µg/mL laminin (laminin derived from Engelbreth-Holm-Swarm murine sarcoma basement membrane: Merck, Cat. No. L2020-1 MG) did not form organoids, as depicted in FIG. 1. Instead, they formed cyst-like structures that died within 2-3 days. Surprisingly, when the extracellular matrix Matrigel® was added to a final concentration of 2.5% budding organoids formed within 3.5 days, although the crypts were not embedded in a sloid matrix but rather in a suspension culture. Notably, this corresponds to a higher growth rate than presented in different publications where organoids are grown in a solid dome of Matrigel®.

Figure 2:
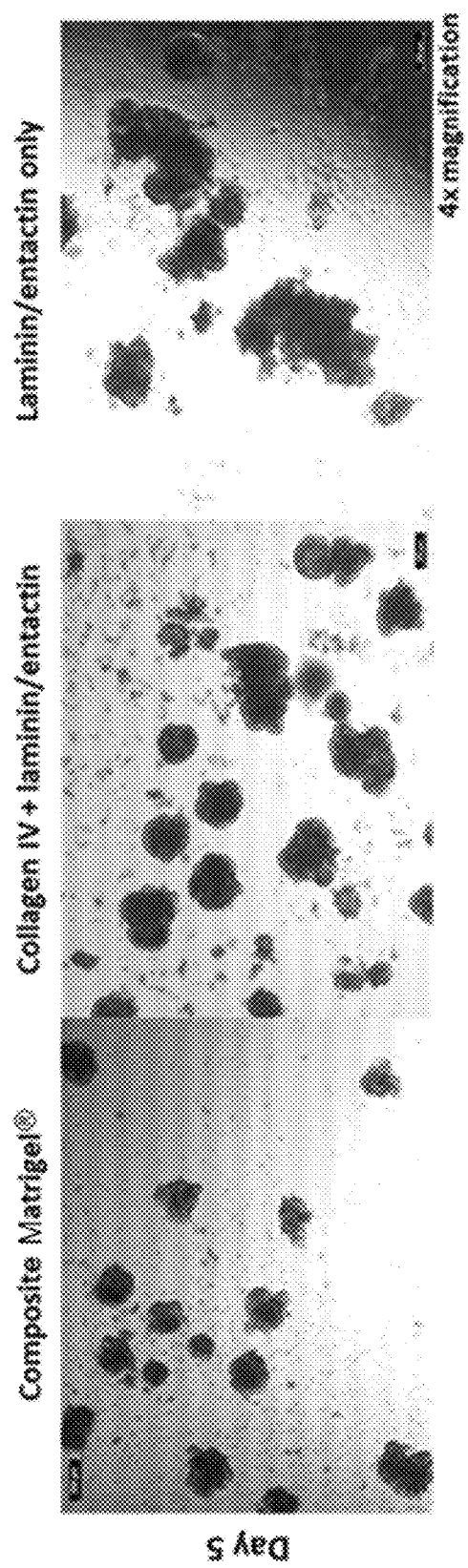
FIG. 2 demonstrates that instead of using the extracellular matrix Matrigel®, also the addition of a combination of collagen, laminin, entactin, fibronectin and hyaluronic acid can function as culture enhancer, yielding crypt-villus organoids. Additionally, also the combination of collagen IV and laminin/entactin complex or laminin/entactin complex alone is sufficient for the generation of organoids in suspension cultures.

Example 2: Laminin/Entactin and EHS Tumor Derived Molecules can Function as Culture Enhancers Matrigel® is a complex, less defined mixture of different ECM components such as collagens and laminins, as well as some growth factors such as EGF. In order to identify components of the Matrigel® supporting formation and growth of small intestinal organoids, crypts were isolated from the small intestine of C57B16 mice and resuspended in small intestinal organoid medium. The crypts were seeded in ultra-low attachment plates. The addition of "composite Matrigel" consisting of collagen, laminin, entactin, fibronectin and hyaluronic acid, mimicking Matrigel addition, lead to the formation of budding organoids. Surprisingly, also the addition of collagen IV and laminin/entactin complex, as well as the addition of laminin/entactin only lead to the formation of budding organoids, as shown in FIG. 2.

Figure 3:
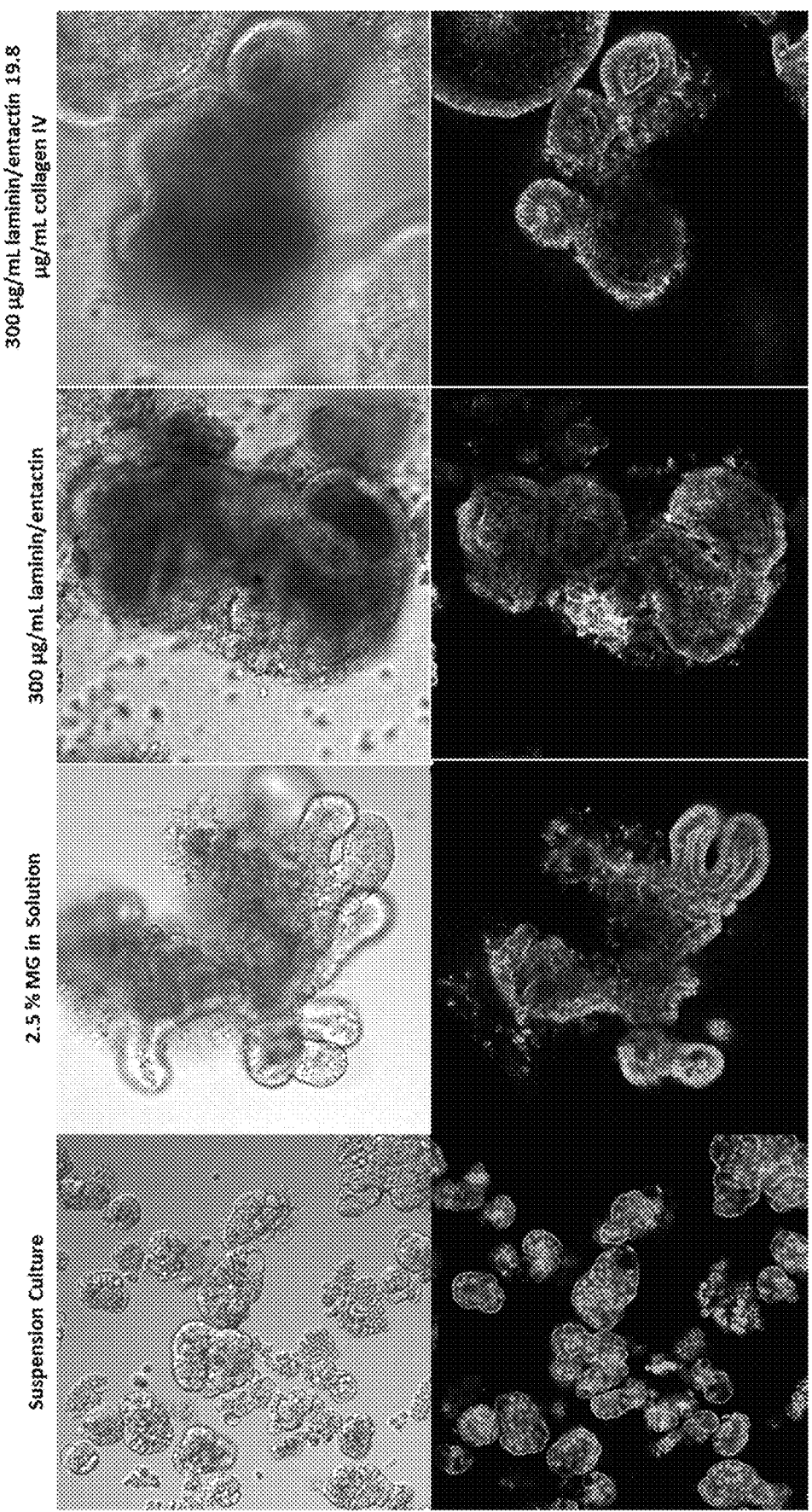
FIG. 3 shows that while crypts cultured in culture medium without embedding in ECM or ECM analogue results in "inside-out" polarization of the forming spheres, the addition of culture enhancers, such as low concentrations of Matrigel®, laminin/entactin complex or the combination of laminin/entactin complex and collagen IV, induces correct polarization and crypt-villus formations in intestinal crypts. Consequently, soluble cultures allow for the generation of organoids in suspension

Example 3: Culture Enhancers Induce Correct Cell Polarization in Suspension Cultures The further characterization of organoids grown in suspension was done by immunofluorescence imaging. Organoids were generated in suspension by only resuspending small intestinal crypts in organoid without adding further components, by adding Matrigel® to a final concentration of 2.5%, by only adding laminin/entactin complex or by adding laminin/entactin complex and collagen IV. The forming budding organoids were fixed with 4% PFA, permeabilized and stained with EpCAM as basal marker, Phalloidin as apical marker and DRAQ5 as marker for nuclei, as shown in FIG. 3. As mentioned before, crypts grown in suspension without further addition of culture enhancers only form cyst-like structures that stop growing and die within 2-3 days. Immunofluorescence analysis revealed that the forming cyst-like structures show an "inside-out" structure with apical markers on the outside of the organoids. However, the addition of culture enhancers induces correct polarization and allows for the formation of budding organoids, as shown by the basal EpCAM staining on the outside of the organoids and the apical Phalloidin staining on the inside directed to the lumen of the organoids.

Figure 4:
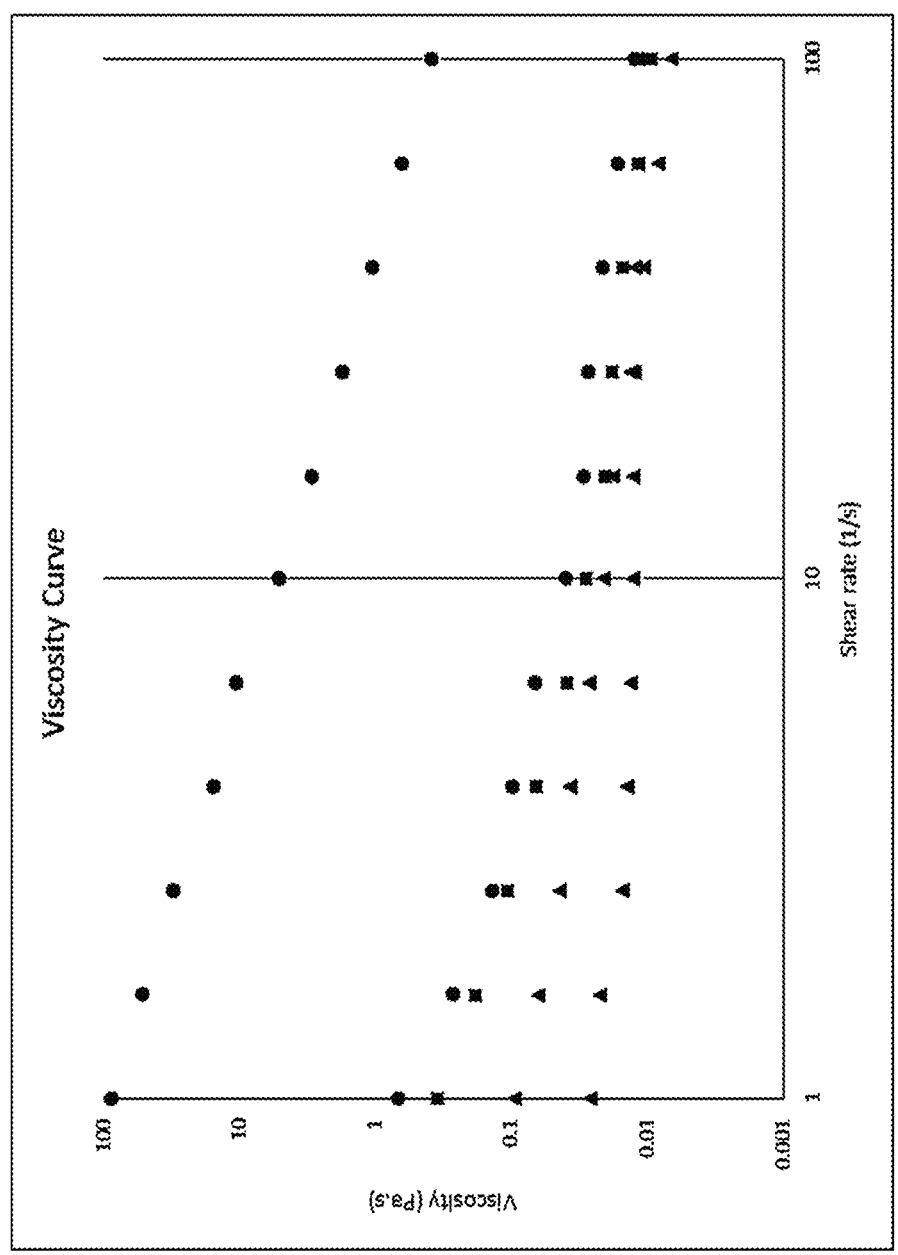
FIG. 4 shows the viscosity curves of culture medium without culture enhancers (DMEM, red), medium containing 2.5% Matrigel® (blue), 10% Matrigel® (green), 20% Matrigel® (orange) and 100% Matrigel® (purple) at 37° C., demonstrating that the culture medium including culture enhancers represents a liquid, suspension medium instead of a semi-solid medium or a hydrogel used for an "embedment" approach. Accordingly, our method uses a liquid medium as defined by an at least approx. 100-fold lower viscosity (Pa at defined shear rate) than Matrigel® in the presented assay.

Example 4: Culture Enhancers do not Significantly Enhance Viscosity of Liquid Media The new method of growing organoids is clearly a contrast to the traditional protocols of growing organoids in a dome of solidified ECMs, since the latter cannot be used to generate real suspension cultures. In order to demonstrate that the cultures are true suspension cultures, the mechanical properties of Matrigel® and medium containing culture enhancers at the needed concentrations were compared by rheology. The mechanical properties of the medium for suspension organoid cultures was compared to DMEM medium without further supplements and Matrigel R by performing an amplitude (1 to 106 shear strain) and frequency sweep (1 to 100 rad/s) both at 37° C. The media were then compared based on viscosity curves as shown in FIG. 4. The data show that DMEM and the suspension organoid medium show comparable curves, while Matrigel R shows a clearly higher viscosity at all plotted shear rates. Our data indicate that the suspension organoid medium is a liquid medium with a comparable viscosity to DMEM rather than a hydrogel as Matrigel R. Accordingly, the new method allows for true suspension cultivation of organoids, rather than relying on embedding cells or tissue pieces in a gel.

Figure 5:
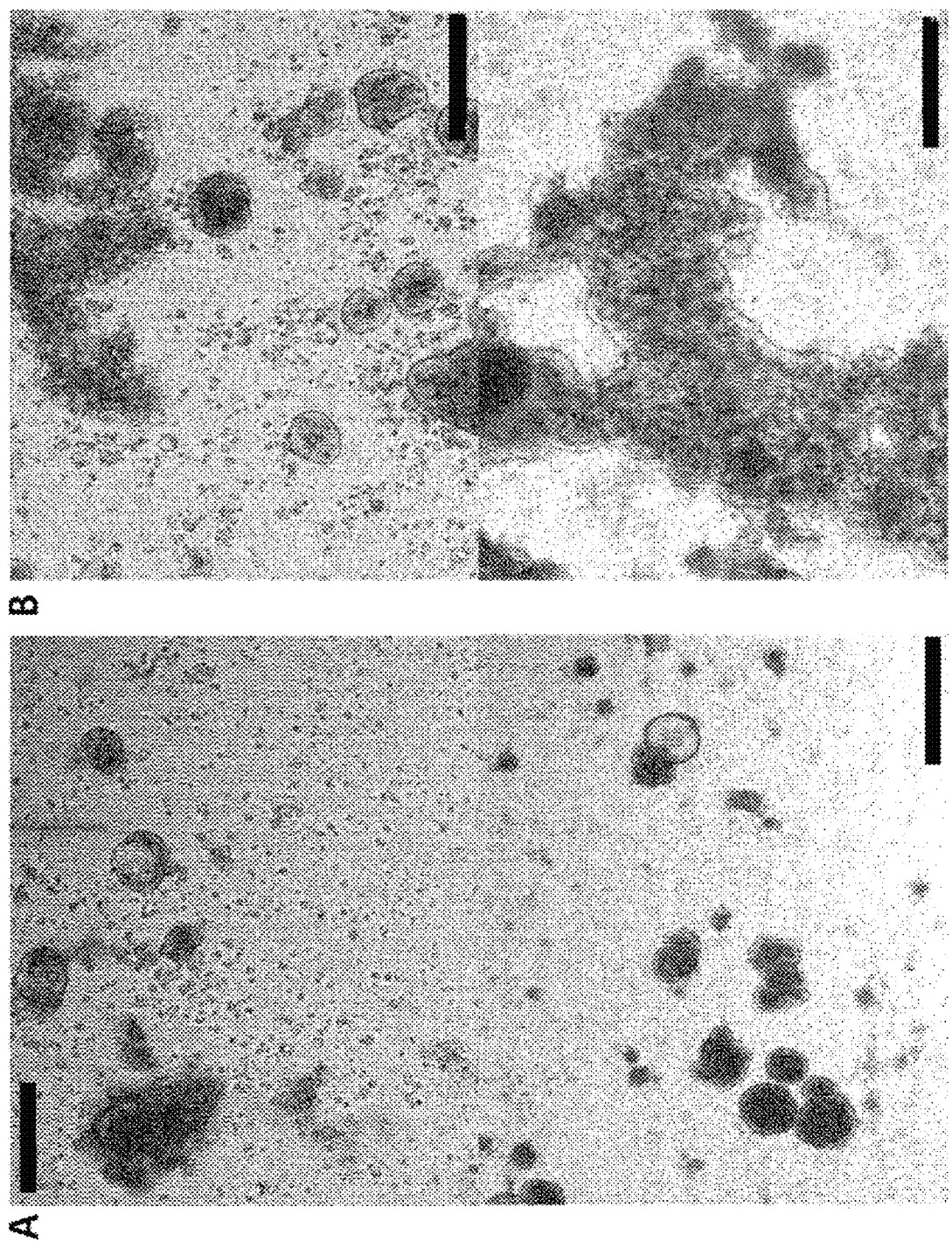
FIG. 5 shows healthy mouse colon (A: 10× magnification) and human colon tumor organoids (B: 10× magnification) generated in suspension by adding culture enhancers to the respective culture medium.

Example 5: Culture Enhancer Promote Organoid Formation in Suspension for Different Epithelial Human and Mouse Tissues In order to prove that the concept of suspension cultivation of organoids using culture enhancers does also work in other tissues, colon crypts were isolated from the colon of C57B16 mice according to published procedures. The crypts were then cultured in ultra-low attachment plates with culture enhancers, as depicted in FIG. 5A. At day 4, colonic crypts had already formed cystic organoids, comparable to those generated in respective publications. In addition, cells from primary human colon carcinoma cell lines were cultured in ultra-low attachment plates in the presence of culture enhancers. Within the first 24 hours, organoid-like structures formed that could be passaged multiple times and continue to grow as organoid-like 3D cultures (see FIG. 5B). This demonstrates that the presence of culture enhancer also allows for suspension cultivation of organoids from other tissues and species.

Example 6: Suspension Cultivation of Organoids Allows for Enhanced Growth Rates

Figure 6:
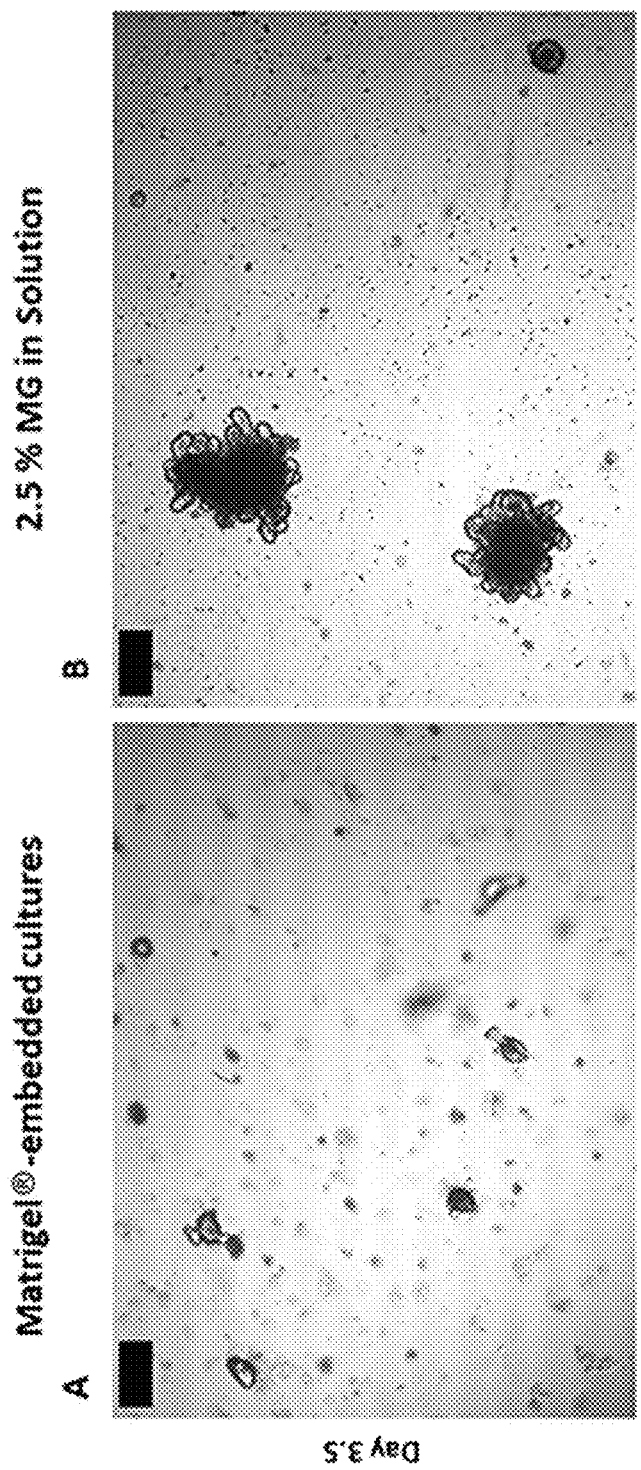
FIG. 6 compares the state of the art embedded organoid culture of intestinal crypts (A) with suspension cultivation using a culture enhancer (B). For both cultures, small intestinal crypts were freshly isolated from the same C57B16 mice and plated according to the respective protocol. At day 3.5, the organoids from both cultures were inspected with the same magnification. This example clearly shows that with standard protocols of embedded cultivation organoids reach a size of approx. 200 µm (diameter) after 3.5 days (A: 10× magnification), while organoids propagated in suspension cultures in the presence of culture enhancers reach a size of approx. 400-650 μm (diameter) within the same time (B: 10× magnification) and using the same cultivation medium.

In order to compare the organoid formation in embedded cultures with organoids generated in suspension cultures in presence of culture enhancers, small intestinal crypts from C57B16 mice were freshly prepared according to published procedures. The crypts were then embedded in a dome of Matrigel® and overlayed with cultivation medium after solidification as depicted in FIG. 6A, or cultured in ultra-low attachment plates with the same cultivation medium with addition of culture enhancers, as shown in FIG. 6B.

After 3.5 days, the size of the organoids was compared by microscopy using the same magnification. Within 3.5 days, following published procedures (FIG. 6A) the organoids grow to a size of approx. 200 µm in diameter and start to form crypt-like domains. Organoids propagated in suspension culture grow to a size of 400-650 µm in diameter within the same time of cultivation. Notably, they also already form multiple crypt-like domains. This suggests an improved and accelerated development rate in suspension cultures. This could potentially speed up protocols for organoid expansion, paving the way for accelerated and facilitated procedures for in vitro screenings for example.

Example 7: Presence of Laminin and Entactin as Complex is Crucial for Suspension Cultivation The main components of EHS tumor-derived matrices like Matrigel® are laminin, collagen IV, entactin, and heparin sulfate proteoglycans. It has been shown that a "composite Matrigel" as well as laminin/entactin with or without collagen IV can induce formation of organoids. To identify the main inducer of organoid formation in suspension cultures, intestinal crypts were isolated from the small intestine of C57B16 mice according to published procedures. The crypts were plated in ultra-low attachment plates with complete culture medium and different ECM molecules also found in Matrigel®.

Figure 7:
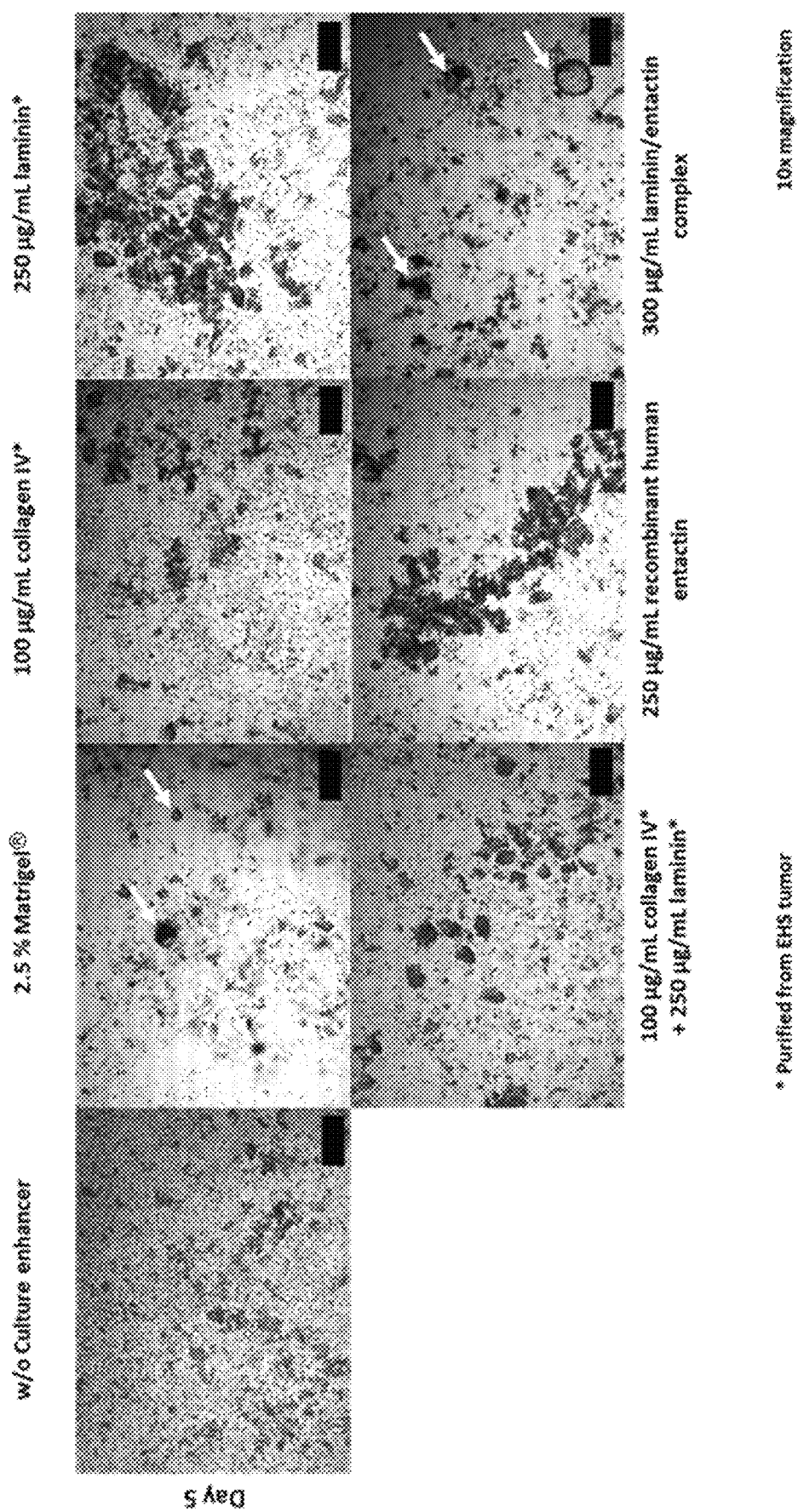
FIG. 7 shows that while crypts cultured in complete culture medium without culture enhancers cannot form and maintain growth as spheres or organoids, the addition of culture enhancers, such as low concentrations of Matrigel® or laminin/entactin complex induces formation of 3D cultures. Consequently, soluble cultures allow for the generation of organoids in suspension. Interestingly, the ECM molecules collagen and laminin, both derived from EHS tumors like Matrigel® or the laminin/entactin complex, alone or in combination also fail to induce formation of organoids in suspension. The same is seen when recombinant entactin is used alone in stead of the complexed form with laminin. Accordingly, this suggests that not any ECM molecules can induce correct polarization and organoid formation, the presence of laminin and entactin as complex is crucial.

As shown in FIG. 7, only a low concentration of Matrigel and the laminin entactin complex were potent to induce organoid formation, while surprisingly entactin alone or collagen IV and laminin derived from EHS tumors alone or in combination failed to induce organoid growth. Surprisingly, this demonstrates that any ECM-derived (glycol) protein alone or in combination are is not sufficient to replace an ECM to allow for organoid formation. Instead, the complex of laminin and entactin is required, while both alone or in combination with another ECM protein also fail to support organoid growth in suspension. This remarkable finding paves the way for the development of more defined protocols for organoid generation and maintenance, as well as to study epithelial cell polarization in more detail.

The invention claimed is:

1. A cell culture for obtaining an epithelial organoid, the cell culture comprising:
   i) epithelial stem cells, or tissue fragments comprising said epithelial stem cells,
   ii) a basal medium for animal or human cells,
   iii) a Bone Morphogenetic Protein (BMP) inhibitor,
   iv) a mitogenic growth factor selected from the group consisting of epidermal growth factor (EGF), transforming growth factor-alpha (TGFα), basic fibroblast growth factor (bFGF), brain-derived neurotrophic factor (BDNF) and keratinocyte growth factor (KGF),
   v) at least one soluble culture enhancer, wherein said at least one culture enhancer induces polarization of the cells in said cell culture that supports development of said epithelial organoid, and
   vi) a Wnt agonist if said epithelial stem cells, or tissue fragments comprising said epithelial stem cells, are healthy cells,
   wherein said at least one soluble culture enhancer in said cell culture is a complex comprising laminin and entactin at a combined concentration between 0.2 mg/mL and 1 mg/mL.

2. The cell culture according to claim 1, wherein said cell culture does not contain a solidified 3D structure apart from said complex comprising laminin and entactin.

3. A cell culture medium for culturing epithelial stem cells, or tissue fragments comprising said epithelial stem cells, for obtaining an epithelial organoid, said cell culture medium comprising:
   i) a basal medium for animal or human cells,
   ii) a Bone Morphogenetic Protein (BMP) inhibitor,
   iii) a mitogenic growth factor selected from the group consisting of epidermal growth factor (EGF), transforming growth factor-alpha (TGFα), basic fibroblast growth factor (bFGF), brain-derived neurotrophic factor (BDNF) and keratinocyte growth factor (KGF),
   iv) at least one soluble culture enhancer, wherein said at least one culture enhancer induces polarization of the cells in said cell culture that supports development of said epithelial organoid, and
   v) a Wnt agonist if said epithelial stem cells, or tissue fragments comprising said epithelial stem cells, are healthy cells,
   wherein said at least one soluble culture enhancer in said cell culture medium is a complex comprising laminin and entactin at a combined concentration between 0.2 mg/mL and 1 mg/mL.

4. The cell culture medium according to claim 3, wherein said cell culture does not contain a solidified 3D structure apart from said complex comprising laminin and entactin.

5. An in vitro method for obtaining an epithelial organoid, the method comprising culturing epithelial stem cells, or tissue fragments comprising said epithelial stem cells in the presence of
   i) a basal medium for animal or human cells,
   ii) a Bone Morphogenetic Protein (BMP) inhibitor,
   iii) a mitogenic growth factor selected from the group consisting of epidermal growth factor (EGF), transforming growth factor-alpha (TGFα), basic fibroblast growth factor (bFGF), brain-derived neurotrophic factor (BDNF) and keratinocyte growth factor (KGF),
   iv) at least one soluble culture enhancer, wherein said at least one culture enhancer induces polarization of the cells that supports development of said epithelial organoid, and
   v) a Wnt agonist if said epithelial stem cells, or tissue fragments comprising said epithelial stem cells, are healthy cells,
   wherein said at least one soluble culture enhancer in said cell culture is a complex comprising laminin and entactin at a combined concentration between 0.2 mg/mL and 1 mg/mL.

6. The in vitro method of claim 5, wherein said at least one soluble culture enhancer is a complex of molecules comprising in parts by weight of 60-85% laminin, 5-30% collagen IV, 1-10% heparan sulfate proteoglycan, and 2-15% entactin at a total concentration between 0.2 mg/mL and 1 mg/mL.

7. The in vitro method according to claim 5, wherein said soluble culture enhancer is initially present during the culturing at a concentration below solidification phase.

8. The in vitro method according to claim 5, wherein said method does not comprise a step of providing a solidified three-dimensional (3-D) structure to said medium apart from said complex comprising laminin and entactin.

9. The in vitro method according to claim 5, wherein the method comprises the step of passaging the cells in said cell culture medium, and wherein said passaging is performed by an automated process.

* * * * *